US00PP22960P2

(12) United States Plant Patent
Clayton

(10) Patent No.: US PP22,960 P2
(45) Date of Patent: Aug. 14, 2012

(54) ***PHLOX* PLANT NAMED 'LORD CLAYTON'**

(50) Latin Name: *Phlox paniculata*
Varietal Denomination: Lord Clayton

(75) Inventor: Tammy Clayton, Mikado, MI (US)

(73) Assignee: Plants Nouveau, LLC, Charleston, NC (US)

( * ) Notice: Subject to any disclaimer, the term of this patent is extended or adjusted under 35 U.S.C. 154(b) by 53 days.

(21) Appl. No.: 12/927,695

(22) Filed: Nov. 22, 2010

(51) Int. Cl.
*A01H 5/00* (2006.01)

(52) U.S. Cl. ..... Plt./320

(58) Field of Classification Search ..... Plt./320
See application file for complete search history.

(56) References Cited

OTHER PUBLICATIONS

Lost in Flower. Tall, Dark and Handsome, retrieved on Feb. 9, 2012. Retrieve from the Internet at <http://lostintheflowers.com/?m=200902> Feb. 2009, pp. 1-25.*

* cited by examiner

*Primary Examiner* — June Hwu
(74) *Attorney, Agent, or Firm* — Penny J. Aguirre

(57) ABSTRACT

A new and distinct cultivar of *Phlox* plant named 'Lord Clayton', characterized by its bushy yet upright plant habit, its strong and almost black colored stems, its deep purple colored leaves in spring, its medium sized and long lasting cherry red colored flowers, and its tolerance to powdery mildew.

2 Drawing Sheets

Botanical classification: *Phlox paniculata.*
Cultivar designation: 'Lord Clayton'.

BACKGROUND OF THE INVENTION

The present invention relates to a new and distinct cultivar of *Phlox* plant, botanically known as *Phlox paniculata* 'Lord Clayton' and will be referred to hereafter by its cultivar name, 'Lord Clayton'. The new cultivar represents a new herbaceous perennial grown for landscape use.

The new cultivar of *Phlox* was discovered as a naturally occurring whole plant mutation in a garden planted with *Phlox paniculata* cultivars by the Inventor in Mikado, Mich. in July 2004. The parentage is unknown.

Asexual reproduction of the new cultivar was first accomplished by stem cuttings in Landenberg, Pa. in 2006 by the Inventor. It has been determined that the characteristics of this cultivar are stable and are reproduced true to type in successive generations.

SUMMARY OF THE INVENTION

The following traits have been repeatedly observed and are determined to be the unique characteristics of 'Lord Clayton'. These characteristics in combination distinguish 'Lord Clayton' as a new and distinct cultivar of *Phlox.*

1. 'Lord Clayton' exhibits a compact and upright plant habit.
2. 'Lord Clayton' exhibits strong stems.
3. 'Lord Clayton' exhibits dark, almost black colored stems throughout the season.
4. 'Lord Clayton' exhibits cherry red colored flowers.
5. 'Lord Clayton' exhibits tolerance to powdery mildew.
6. 'Lord Clayton' exhibits leaves that emerge deep purple with green veins in spring and changing to green with a purple flush in summer.

The new *Phlox* can be compared to *Phlox paniculata* 'Starfire' (un-patented). Plants of the new *Phlox* and 'Starfire' differ primarily in the following characteristics: 1. The new *Phlox* has darker-colored foliage than 'Starfire'. 2. Flowers of the new *Phlox* are deeper cherry red in color than the flowers of 'Starfire'. 3. The new *Phlox* is more tolerant to powdery mildew than 'Starfire'.

The new *Phlox* can also be compared to *Phlox paniculata* 'Sandra', (un-patented). Plants of the new *Phlox* and 'Sandra' differ primarily in the following characteristics: 1. The new *Phlox* has darker-colored foliage than 'Sandra'. 2. The new *Phlox* has more flowers per inflorescence than 'Sandra'. 3. The new *Phlox* is more tolerant to powdery mildew than 'Sandra'.

BRIEF DESCRIPTION OF THE DRAWING

The accompanying colored photographs illustrate the overall appearance and distinct characteristics of the new *Phlox*. The photographs were taken of a three year-old plant of 'Lord Clayton' as grown in a garden in Landenberg, Pa.

The photograph in FIG. 1 comprises a side perspective view of a typical plant of 'Lord Clayton' in early summer.

Figure 1:
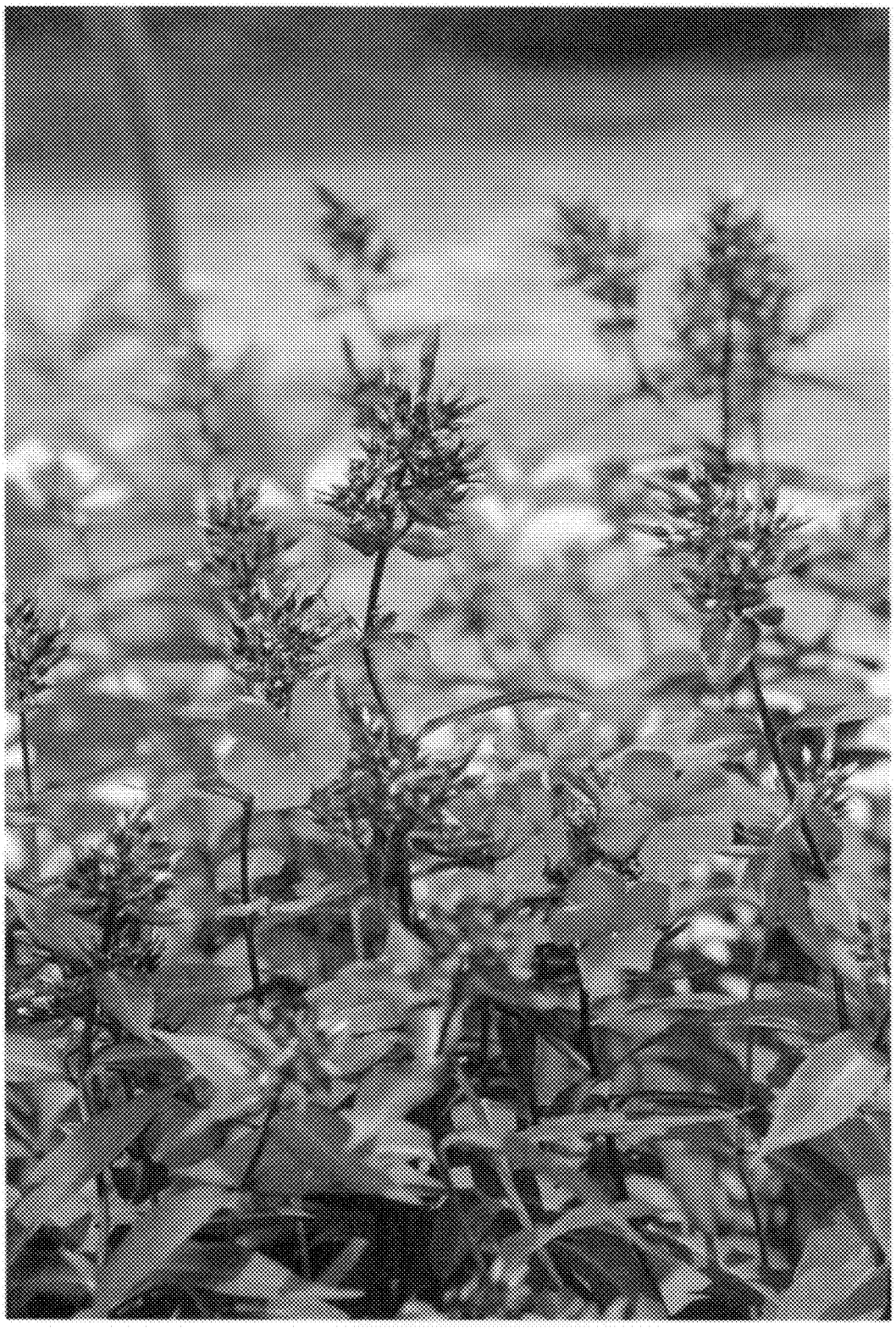
Figure 2:
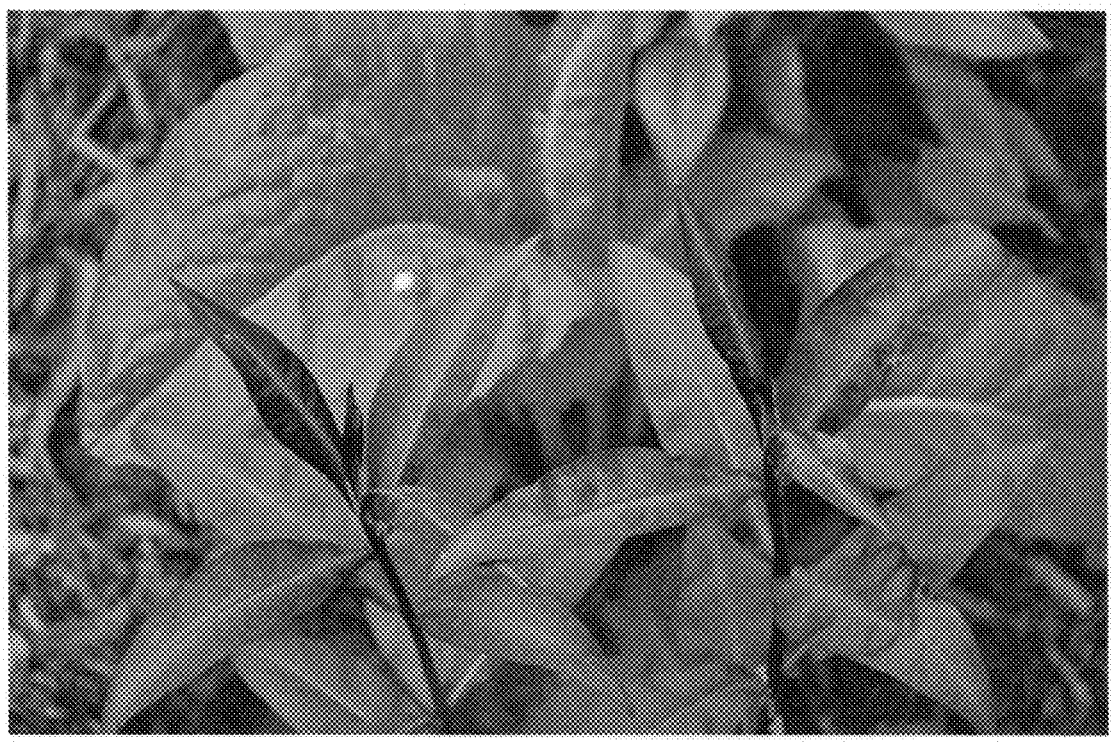

The photograph in FIG. 2 provides a close-up view of typical leaves of 'Lord Clayton' in spring.

Figure 3:
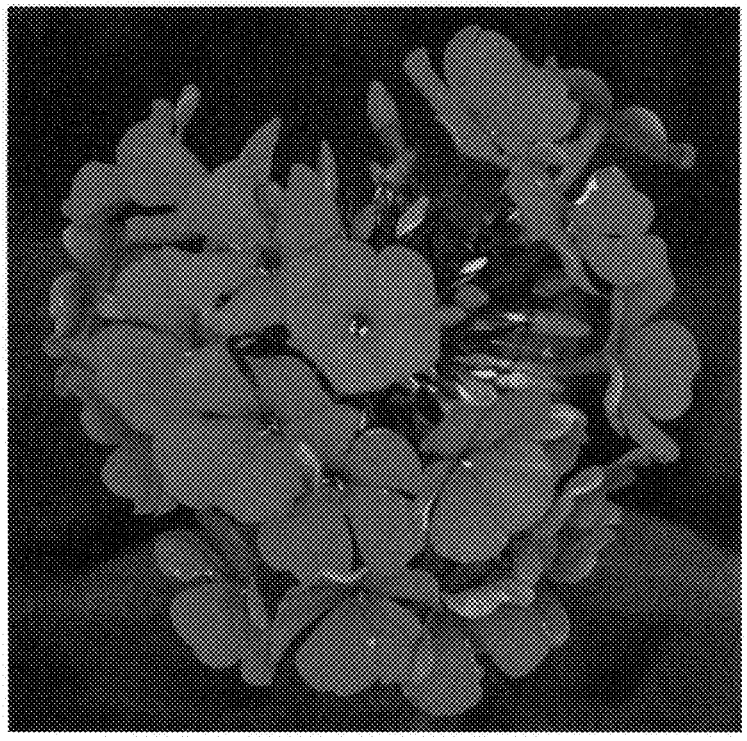

The photograph in FIG. 3 provides a close-up view of typical flowers and buds of 'Lord Clayton' in mid summer.

The colors in the photograph may differ slightly from the color values cited in the detailed botanical description, which accurately describe the colors of the new *Phlox.*

DETAILED BOTANICAL DESCRIPTION OF THE PLANT

The following is a detailed description of three year-old plants of the new cultivar as grown outdoors in a garden in Baltimore, Md. The plants were grown under average day temperatures of 23° C. to 40° C. and average night temperatures of 15° C. to 32° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Continuously from June to August in Baltimore, Md.

*Plant habit*.—Herbaceous perennial, compact, upright.

*Height and spread*.—Reaches about 75 cm in height and about 60 cm in spread.

*Hardiness*.—Tolerant to temperatures ranging from −20° C. to 40° C.

*Environmental stresses*.—Good garden performance with tolerance to rain and wind.

*Diseases and pests*.—Has shown good resistance to powdery mildew and no particular resistance or susceptibility to pests.

*Root description*.—Moderate branching, dense, fibrous.

Growth and propagation:

*Growth rate*.—Moderate.

*Propagation*.—Stem cuttings.

*Time to initiate roots*.—About two weeks at 15° C. to 25° C.

*Time to produce a rooted young plant*.—About 35 days at 15° C. to 25° C.

Stem description:

*Stem size*.—An average of 31 cm in length and 3 mm in width.

*Stem shape*.—Round.

*Stem strength*.—Strong and sturdy.

*Stem color*.—Close to N186C throughout the growing season.

*Stem surface*.—Glabrous, smooth.

*Stem aspect*.—Held nearly upright.

*Internode length*.—An average of 4 cm.

*Branching habit*.—Flowering stems emerge from crown, an average of 5 stems per plant three years in age, pinching enhances branching.

Foliage description:

*Leaf shape*.—Narrowly ovate to elliptic.

*Leaf division*.—Simple.

*Leaf base*.—Obtuse.

*Leaf apex*.—Narrowly acute.

*Leaf venation*.—Pinnate.

*Leaf margins*.—Very finely serrate.

*Leaf attachment*.—Petiolate.

*Leaf arrangement*.—Opposite.

*Leaf size*.—An average of 10 cm in length and 4 cm in width.

*Leaf fragrance*.—None.

*Leaf surface*.—Smooth and glabrous on upper and lower surface.

*Leaf color*.—Developing leaves upper surface; about N186B with venation close to 144A, developing leaves lower surface; about N186B, fully expanded leaves upper surface; close to 144A with N187A blushings, venation close to 144C, fully expanded leaves lower surface; close to 144A, venation close to 144C.

*Petioles*.—Length; about 7 mm, diameter; about 1 mm, texture, upper and lower surfaces; smooth, glabrous, color, upper and lower surfaces; close to 143B.

Flower description:

*Inflorescence type*.—Compound terminal panicle of single rotate flowers, panicle rounded in shape.

*Lastingness of inflorescence*.—About 4 weeks from the opening of the first flower to senescence of last flower, individual flower lasts about 10 days, not persistent.

*Inflorescence size*.—An average of 9 cm in height and 10 cm in diameter.

*Flower fragrance*.—Moderate, sweet and flowery.

*Flower number*.—Average of 80 per inflorescence, one inflorescence per flowering stem.

*Flower aspect*.—Primarily outward.

*Flower bud*.—An average of 1.4 cm in length and up to 3 mm in width, narrow oblanceolate in shape, between 71C and 71D in color.

*Flower form*.—Explanate with tubular base.

*Flower size*.—An average of 2.8 cm in length and 3.2 cm in diameter.

*Corolla tube*.—About 1.5 cm in length, 2.5 mm in width, developing flowers; close NN155B with striations of 67B, mature flowers; 72B, smooth surface.

*Corolla lobes*.—5, roughly spatulate in shape, held horizontally when fully open, slightly overlapping, about 1 cm in length and width, apex rounded, base fused to tube, entire margins, color developing petals, upper surface; close to 52A with striations close to N66A, towards the throat, close to N57B, developing petals, lower surface; 58D with a few minor spots of 155B; fully expanded petals, upper surface; close to N78A; spots, between 76D and N155A; towards the throat, darker than 67A, fully expanded petals, lower surface; 53D, surface is smooth on upper and lower surface.

*Sepals*.—5, fused towards base, lanceolate in shape, margins entire, apex narrowly apiculate, an average of 6 mm in length and 1.7 mm in width, surface is smooth and glabrous on upper and lower surface, color on developing flowers; upper surface close to N77A, lower surface close to 143C, color of fully open flowers upper and lower surface; N77A with blushings of 142B.

*Peduncles*.—Length; about 6 cm, diameter; about 3 mm, strength; strong, texture; smooth, glabrous, color; 144C with striations of N79B.

*Pedicels*.—Length: about 5 mm, diameter; about 1 mm, strength; strong, texture; smooth, glabrous, color: close to 144B.

Reproductive organs:

*Gynoecium*.—1 pistil, about 10 mm in length, stigma is three parted and 140A in color, style is about 3 mm in length and close to 140A in color, ovary is inferior and 140A in color.

*Androcoecium*.—Typically 5 stamens, anthers are basifixed, oblong in shape, 2 mm in length and 155B in color, filaments are about 8 mm in length, pollen is moderate in quantity and close to 140A in color.

*Seeds*.—Development has not been observed.

It is claimed:

1. A new and distinct cultivar of *Phlox* plant named 'Lord Clayton' as herein illustrated and described.

* * * * *